(12) United States Patent
Atkinson et al.

(10) Patent No.: US 11,305,075 B2
(45) Date of Patent: Apr. 19, 2022

(54) NASAL MEDICATION DELIVERY DEVICE (71) Applicant: AFT Pharmaceuticals Limited, Auckland (NZ)

(72) Inventors: Hartley Campbell Atkinson, Auckland (NZ); Brendon John Woodhead, Auckland (NZ)

(73) Assignee: AFT PHARMACEUTICALS LIMITED, Auckland (NZ)

( * ) Notice: Subject to any disclaimer, the term of this patent is extended or adjusted under 35 U.S.C. 154(b) by 0 days.

(21) Appl. No.: 15/553,801

(22) PCT Filed: Jan. 8, 2016

(86) PCT No.: PCT/NZ2016/050002
§ 371 (c)(1),
(2) Date: Aug. 25, 2017

(87) PCT Pub. No.: WO2016/163895
PCT Pub. Date: Oct. 13, 2016

(65) Prior Publication Data
US 2018/0036498 A1    Feb. 8, 2018

(30) Foreign Application Priority Data
Apr. 9, 2015   (NZ) ..................................... 706864

(51) Int. Cl.
*A61M 15/00*   (2006.01)
*A61M 11/00*   (2006.01)
(Continued)

(52) U.S. Cl.
CPC ...... *A61M 15/0098* (2014.02); *A61M 11/005* (2013.01); *A61M 15/0085* (2013.01);
(Continued)

(58) Field of Classification Search
CPC .......... A61M 15/0098; A61M 15/0085; A61M 15/08; A61M 2205/3375;
(Continued)

(56) References Cited

U.S. PATENT DOCUMENTS

| | | | | |
|---|---|---|---|---|
| 3,387,607 A | * | 6/1968 | Gauthier | B05B 17/0638 128/200.16 |
| 6,705,312 B2 | * | 3/2004 | Tanaka | A61M 15/00 128/200.14 |

(Continued)

FOREIGN PATENT DOCUMENTS

| WO | WO2004045690 | 6/2004 |
|---|---|---|
| WO | 2007028203 A1 | 3/2007 |
| WO | WO2013132427 | 9/2013 |

OTHER PUBLICATIONS

Int'l Search Report and Written Opinion for Int'l Patent App. No. PCT/NZ2016/050002, dated Apr. 15, 2016, 13 pages, Australian Patent Office, International Bureau.

(Continued)

*Primary Examiner* — Elliot S Ruddie
(74) *Attorney, Agent, or Firm* — Douglas J. Ryder; Ryder, Mazzeo & Konieczny LLC (57) ABSTRACT

The invention relates to a delivery device for nasal medication. It addresses need for delivering medication to the nose of a patient. In a preferred embodiment the device has: •A transducer 10 adapted to create an ultrasonic focal zone; •a feeder chamber 13 holding medication; •an energising chamber 14 smaller than the feeder chamber; •a mesh 15; and •an exit 17. The device is formed so that when it is activated the feeder chamber 13 continuously fills the energising chamber 14 with medication (until the feeder chamber has insufficient medication left to achieve this) so that there is a substantially constant supply of medication within (51) Int. Cl.
*A61M 15/08* (2006.01)
*B05B 17/00* (2006.01)

(52) U.S. Cl.
CPC ......... *A61M 15/08* (2013.01); *B05B 17/0638* (2013.01); *A61M 2205/3375* (2013.01); *A61M 2205/502* (2013.01); *A61M 2205/6018* (2013.01); *A61M 2205/6054* (2013.01); *A61M 2205/8206* (2013.01); *A61M 2205/8237* (2013.01)

(58) Field of Classification Search
CPC .... A61M 2205/502; A61M 2205/6018; A61M 2205/6054; A61M 2205/8206; A61M 2205/8237; A61M 11/005; B05B 17/00; B05B 17/04; B05B 17/06; B05B 17/0607; B05B 17/0615; B05B 17/0623; B05B 17/063; B05B 17/0638; B05B 17/0646; B05B 17/0653–0684
See application file for complete search history.

(56) References Cited

U.S. PATENT DOCUMENTS

| | | | |
|---|---|---|---|
| 7,347,201 B2 | 3/2008 | Djupesland | |
| 7,426,866 B2* | 9/2008 | Van Tuyl | G01N 29/024 73/597 |
| 7,721,729 B2* | 5/2010 | Von Hollen | A61M 15/0085 128/200.14 |
| 2006/0201502 A1* | 9/2006 | Lieberman | A61M 11/005 128/204.14 |
| 2006/0243274 A1* | 11/2006 | Lieberman | A61M 11/005 128/200.14 |
| 2008/0022395 A1 | 1/2008 | Holtzman | |
| 2008/0156320 A1* | 7/2008 | Low | A61M 11/005 128/200.16 |
| 2008/0223953 A1* | 9/2008 | Tomono | F24F 6/12 239/102.2 |
| 2008/0245362 A1* | 10/2008 | Moessis | A61M 15/0085 128/200.16 |
| 2009/0200397 A1* | 8/2009 | Sheiman | B05B 17/0607 239/102.2 |
| 2010/0023654 A1 | 1/2010 | Ramsdale | |
| 2011/0012045 A1 | 1/2011 | Schaefer et al. | |
| 2011/0120456 A1* | 5/2011 | Immel | A61M 15/0085 128/200.23 |
| 2013/0112197 A1 | 5/2013 | Kruener et al. | |
| 2014/0025133 A1 | 1/2014 | Lozano | |
| 2014/0352689 A1 | 12/2014 | Seshadri et al. | |
| 2016/0058960 A1* | 3/2016 | Papania | A61B 1/00195 600/103 |

OTHER PUBLICATIONS

Int'l Preliminary Reporton Patentability for Int'l Patent App. No. PCT/NZ2016/050002, dated Jun. 14, 2017, 19 pages, Australian Patent Office, International Bureau.

* cited by examiner

NASAL MEDICATION DELIVERY DEVICE

FIELD OF INVENTION

This invention relates to a device for delivering medication to the nasal cavity of a human patient.

BACKGROUND

Devices which deliver medication to the nasal cavities are known. In some cases they create an aerosol from liquid medication using compressed gas or piezoelectric energy. They are often referred to as "nebulisers" and they typically have a chamber in which the medication is energised. The medicament is then caused to contact a mesh, or to move through a jet nozzle, to enter the nasal cavities as an aerosol. The mesh may be vibrated directly via a piezo-oscillating element, or indirectly as a result of acoustic energy. The acoustic energy may also be used to drive the medication to the mesh.

Some nebulisers have a drawback in that their delivery mechanism requires an undesirably large minimum volume of medication before they can do their work. When the medication falls to below that volume a relatively large residual amount is wasted. It is an object of a preferred embodiment of the present invention to go at least some way towards alleviating this problem. However this and any other objects of the preferred embodiment should not be taken as a limitation on the scope of the invention or claims. The object of the invention in its broadest form is simply to provide a useful choice.

SUMMARY OF THE INVENTION

According to one aspect of the invention there is provided a delivery device for nasal medication, having:
   an ultrasonic energy generator adapted to create an ultrasonic focal zone;
   a feeder chamber holding medication;
   an energising chamber smaller than the feeder chamber;
   a mesh; and
   an exit;
the device formed so that when it is activated the feeder chamber continuously fills the energising chamber with medication (until the feeder chamber has insufficient medication left to achieve this) so that there is a substantially constant supply of medication within the focal zone able to be energised and forced from the energising chamber so as to contact the mesh, become an aerosol, and leave the device by way of the exit.

Optionally the device has a mouthpiece adapted for a human user to blow into and sensing means which, in response to such blowing, causes the medication to be energised and the aerosol to form.

Optionally the energising chamber has a volume of 0.1 cm$^3$ to 0.8 cm$^3$, and preferably a volume of 0.2 cm$^3$ to 0.4 cm$^3$.

Optionally the ultrasonic generator comprises a concave transducer adapted to focus ultrasonic energy on the focal zone when activated, such that the medication in the energising chamber becomes acoustically energised and moves towards the mesh.

Optionally the device is formed such that it causes the mesh to vibrate as the medication contacts it so as to assist in creating the aerosol.

Optionally the device has a nasal prong and the exit is part of the prong.

Optionally the mesh is integral with the prong.

Optionally the mesh is immediately adjacent to the exit so as to prevent or minimise condensation of the aerosol inside the device.

Optionally the energising chamber, the generator and exit are at an angle of about 40° to about 80°, and preferably about 50° to about 70°, with respect to the mouthpiece.

Optionally the medication is a pharmaceutical or saline solution prior to being energised.

Optionally the feeder chamber has a funnel or flume formed to naturally encourage the medication into the energising chamber.

Optionally the energising chamber has a tapered floor to urge medication to gather at the focal zone.

Optionally the energising chamber has a well to urge medication to gather at the focal zone.

Optionally the energising chamber is symmetrical.

Optionally the energising chamber is asymmetrical.

Optionally the feeder chamber plus the energising chamber collectively have sufficient medication for:
   only 5 or fewer patient doses;
   only 4 or fewer patient doses;
   only 3 or fewer patient doses;
   only 2 or fewer patient doses; or
   only 1 patient dose;
(a dose in this context is the amount of medication per administration event, as opposed to, for example, the number of acoustic pulses needed to dispense that amount)(the energising chamber may, in some embodiments, be initially empty).

According to a further aspect f the invention there is provided a delivery device for nasal medication, having:
   a mouth piece;
   sensing means;
   an ultrasonic energy generator in the form of a concave transducer adapted to focus ultrasonic energy on a focal zone;
   a feeder chamber holding medication;
   an energising chamber smaller than the feeder chamber;
   a mesh; and
   a nasal prong;
   the device formed so that when it is activated the feeder chamber continuously fills the energising chamber with medication (until the feeder chamber has insufficient medication left to achieve this) so that there is a substantially constant supply of medication within the focal zone able to be energised and forced from the energising chamber so as to contact the mesh, become an aerosol, and leave the device by way of the nasal prong;
   the sensing means arranged to detect when a user blows into the mouth and to then cause the medication to be energised while the mesh oscillates to produce a pumping action to assist in creating the aerosol;
   the feeder chamber having a funnel or flume formed to encourage the medication into the energising chamber; and
   the energising chamber having a tapered floor and/or well arranged to urge the medication into the focal zone.

DESCRIPTION OF THE DRAWINGS

Some preferred embodiments of the invention will now be described by way of example and with reference to the accompanying drawings, of which.

DETAILED DESCRIPTION

Figure 1:
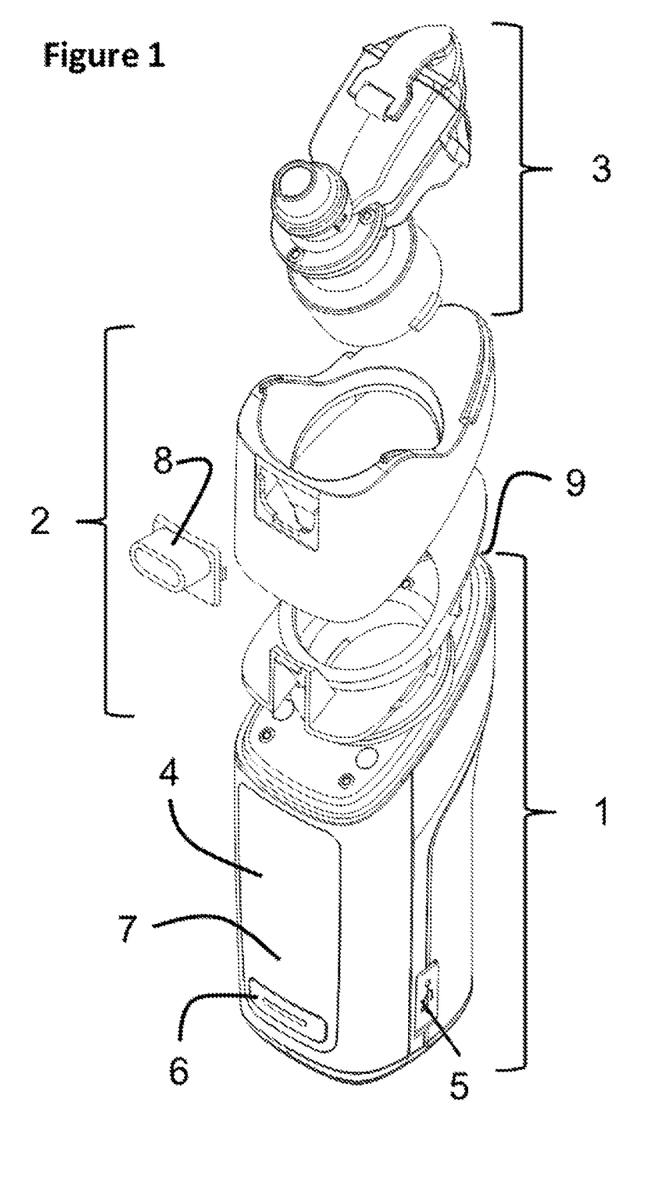
FIG. 1 is an exploded isometric view of a nasal medication delivery device.

Referring to FIG. 1, the delivery device is used for the administration of therapeutic agents to the nasal cavity of a human patient. It has a main body 1, a breath receptor 2, and a medicine supply unit 3.

The Main Body

The main body 1 has an LCD screen 4 to display messages to the user, for example the name of the medicine to be delivered, the time at which the next dose is due to be taken, etc. The main body 1 also has a battery, a USB port 5 for charging the battery or for receiving input generally, an on/off power switch 6, an RFID reader 7 and a breath sensor. All of the electronics for the delivery device are part of the main body 1.

The RFID reader 7 is able to read electronically stored prescription details kept on a tag on the medicine packaging. Those details are used to automatically set the device to deliver the prescribed amount of medicine.

The Breath Receptor

The breath receptor 2 is detachable from the main body 1 with a click-fit arrangement, and has a detachable replaceable mouthpiece 8. The mouthpiece 8 can be gripped between the lips of the user and blown into. As the breath moves through the receptor 2 it is acoustically detected by the sensor in the main body 1, and, as a consequence, the device is triggered to deliver medicine to the user. The breath then passes out the back 9 of the device, having served its purpose. The device only releases medicine while the user is blowing/exhaling. This is because the act of exhaling causes the user's pharynx to close, so that medicine is only delivered to the nose, and not the throat or lungs.

The Medicine Supply Unit

Referring to FIGS. 2 to 6, the medicine supply unit 3 has a concave piezo-ceramic ultrasonic transducer 10, ultrasonic energy transmission fluid 11 (optionally water), an ultrasonic transparent membrane 12 (which may be formed from a material such as polyetheretherketone (PEEK)), a medicine (liquid) feeder chamber 13, a liquid energising chamber 14, a mesh 15 and a nasal prong 16. The energising chamber 14 may or may not be asymmetrical or angled. The nasal prong 16 and a sub-assembly of the mesh engage the rest of the supply unit 3 by way of a twist lock mechanism to enable it to be easily cleaned or replaced.

Figure 4:
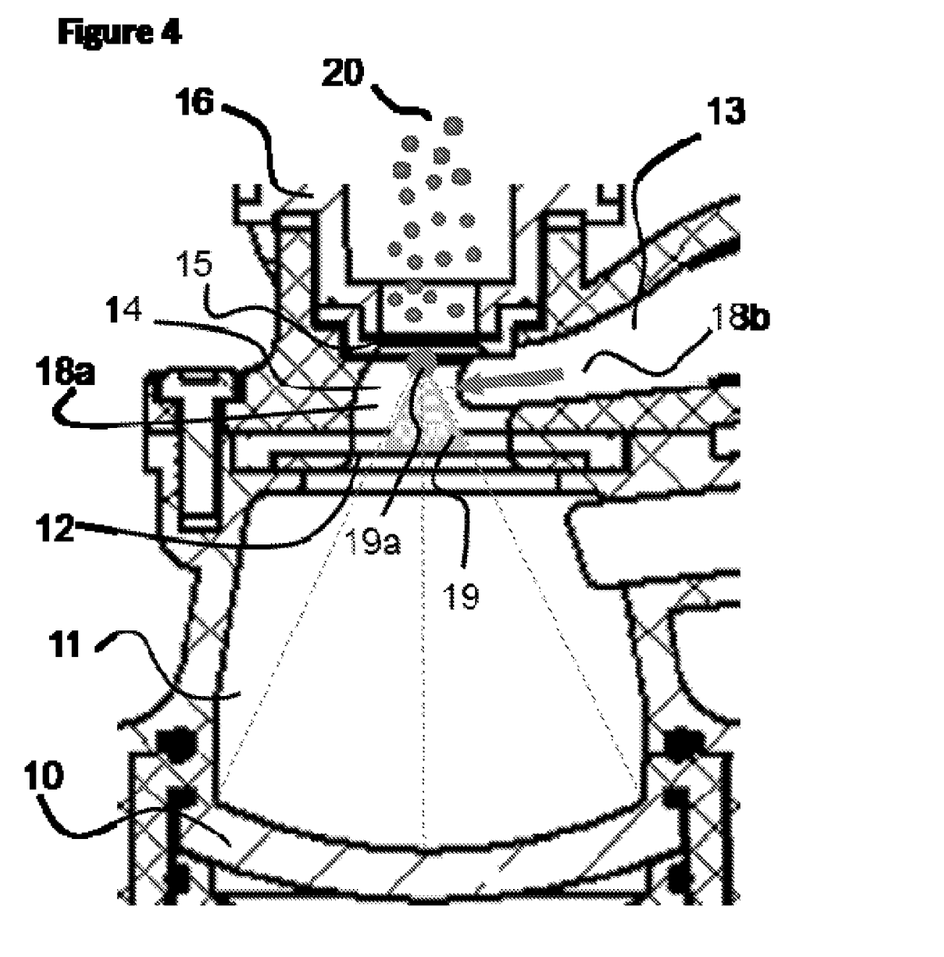
FIG. 4 is an expanded side cross-sectional view showing detail of the supply unit.
Figure 5:
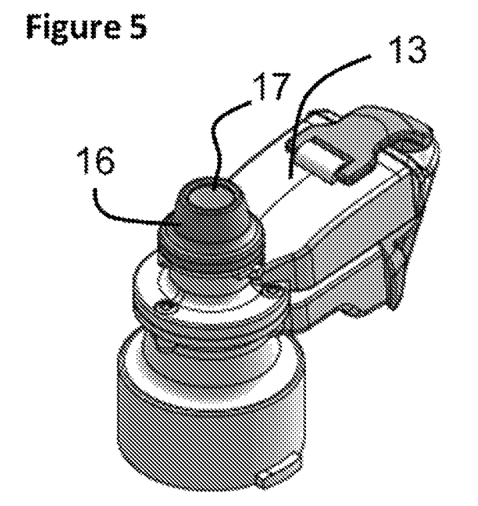
FIG. 5 is an isometric view of the supply unit.
Figure 6:
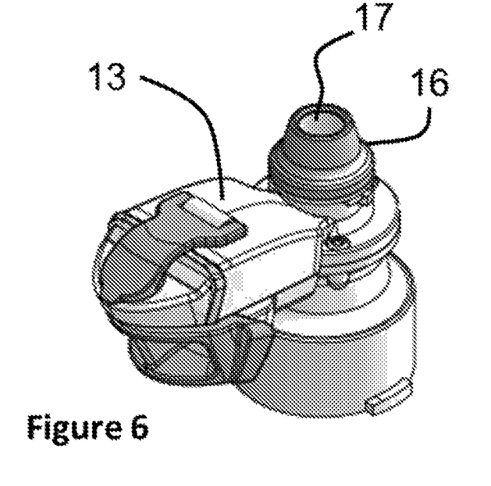
FIG. 6 is an opposite isometric view of the supply unit.

With particular reference to FIG. 4, the transducer 10 is concave and emits ultrasonic energy that travels through the transmission fluid 11, through the membrane 12 and into a charge of medicine 18a in the energising chamber 14. The charge 18a becomes acoustically energized within an acoustic focal zone 19 created by the transducer, which produces an acoustic radiation pressure on the inner face of the mesh 15. As a result the mesh 15 oscillates and produces a micro-pumping action of the medicine as it moves through the pores of the mesh 15. Such contact with the mesh 15 causes the medicine to become an aerosol 20, ie at the outer face of the mesh 15. The aerosol 20 then passes out of the nasal prong 16 via the exit 17. If the prong is held in the user's nose the aerosol enters his or her nasal cavity to give therapeutic relief.

With further reference to FIG. 4, the concave nature of the transducer 10 concentrates ultrasonic energy at the focal zone 19 within the energising chamber 14 so that the charge of medicine 18a becomes acoustically activated. The dotted lines in FIG. 4 illustrate an ultrasonic energy pathway resulting from the concavity of the transducer 10. The area referred to as the focal zone 19 is a small region of concentrated ultrasonic energy. As indicated, the focal zone preferably incorporates the focal point 19a, the position of which is dependent on the curvature of the transducer. In some embodiments of the invention the focal zone may be equivalent to the focal point.

In the preferred embodiment the energising chamber 14 is approximately 0.2 $cm^3$ to 0.4 $cm^3$ in size. The small size of the energising chamber 14 with respect to the liquid storage chamber 13 means that the size of the focal zone 19 is minimised. This helps to minimise or substantially limit the amount of residual medicine (wastage) in the energising chamber 14 when the feeder chamber is exhausted.

The liquid medicine 18a in the energising chamber 14 is replenished with a new charge of medicine 18b under normal gravity from the feeder chamber 13. This ensures that there is always a charge of medicine 18a ready to be acoustically energized, that is until the medicine in the liquid storage chamber is emptied. When there is insufficient volume of medicine in the energising chamber 14 there will not be enough acoustic radiation pressure to effectively oscillate the mesh 15.

Figure 2:
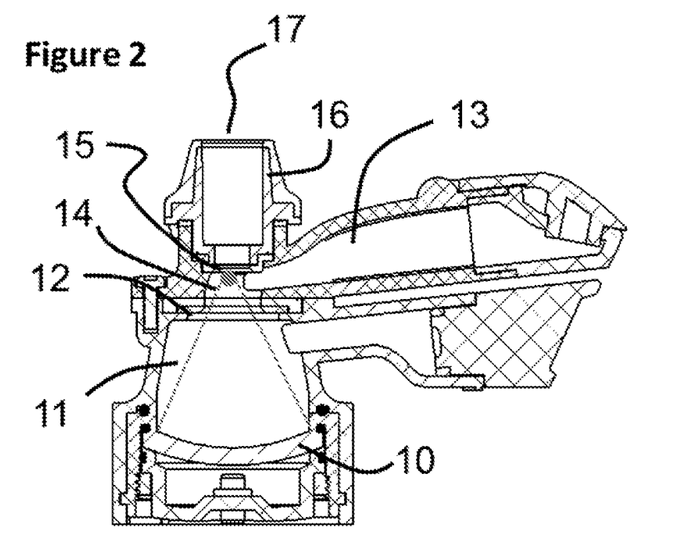
FIG. 2 is a side cross-sectional view of the supply unit.
Figure 3:
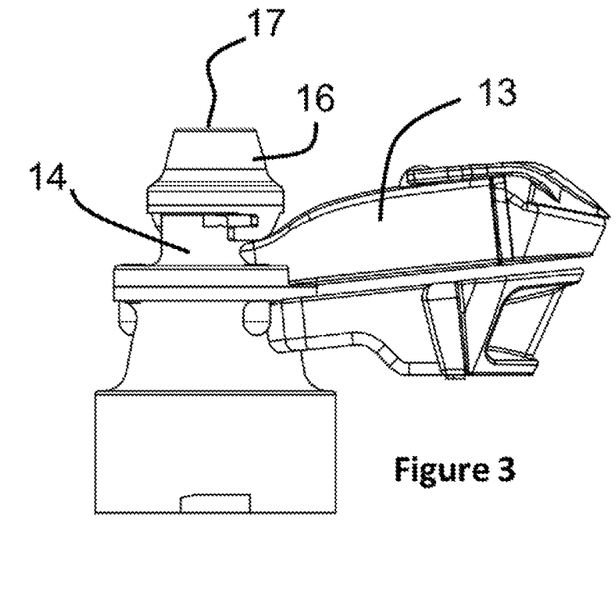
FIG. 3 is a side view of the exterior of the supply unit.

Referring to FIG. 2, the mesh 15 is located within and is integral with the nasal prong 16, and the exit is an opening 17 at the end of the prong. The pore size of the mesh 15 determines, in part, the size of the aerosol droplets.

Figure 7:
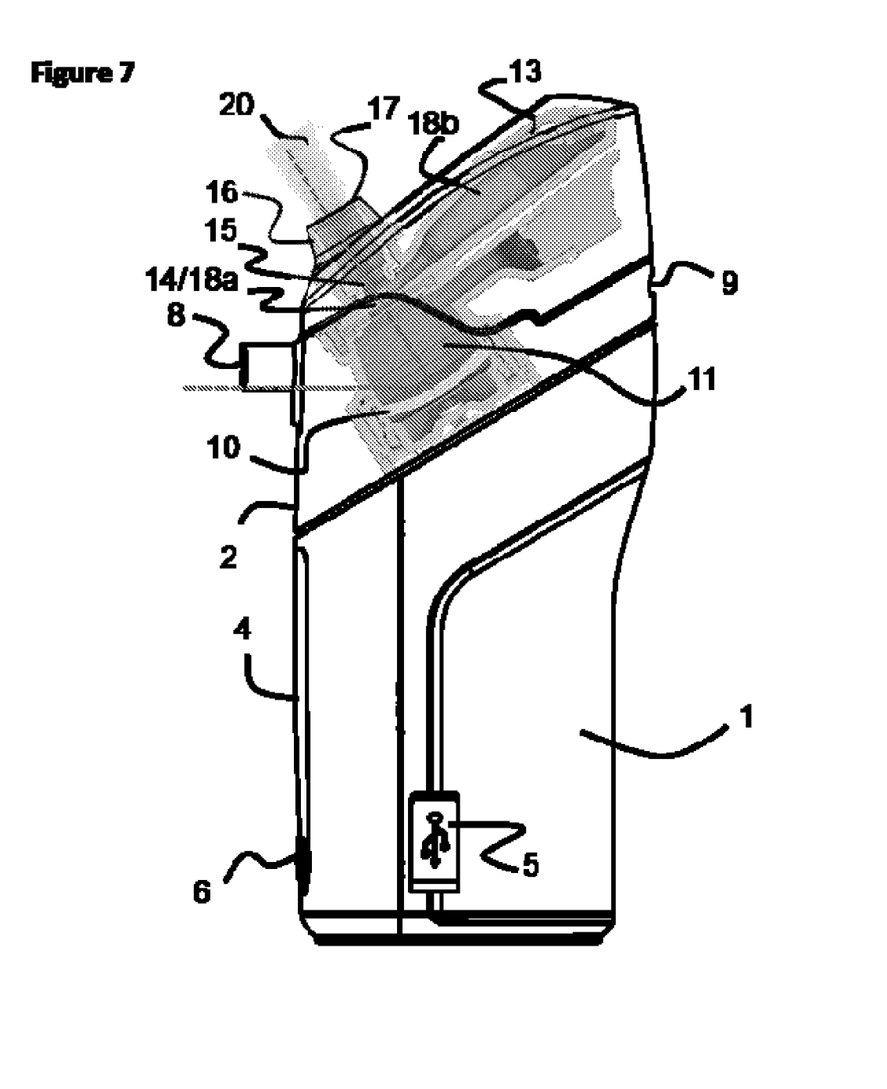
FIG. 7 is schematic part cross-sectional view, and exterior view, of the device illustrating angled placement of various parts.

Referring to FIG. 1, the medicine supply unit 3 can be readily detached from the main body 1 for cleaning, disinfection or replacement altogether. It connects to the body 1 via a cavity in the breath receptor 2. With particular reference to FIG. 7, the medicine supply unit is angled slightly upwards to help the medicine flow more easily into the energising chamber 14 and to prevent bubbles forming in either the energising chamber or the transmission media 11. The angle also assists one to better align the path of aerosol leaving the mesh with targeted areas within the nasal cavity.

Other Features

In some embodiments of the invention the device will only run if the user has purchased sufficient electronic 'credits', which are communicated to the device wirelessly or by hardwire.

Figure 8:
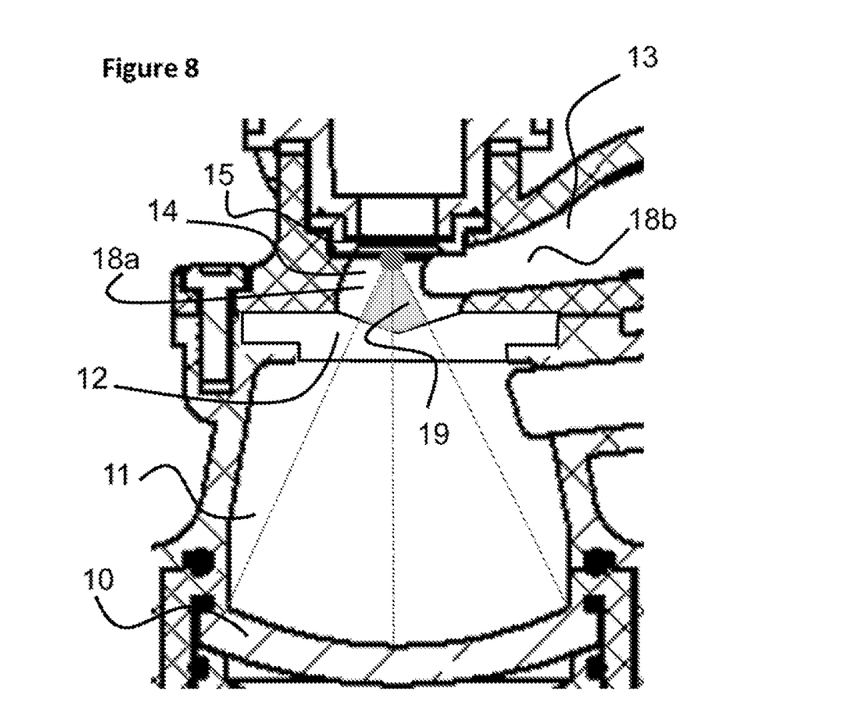
FIG. 8 is a side cross-sectional view showing detail of the medicine supply unit of an alternative embodiment of the invention showing a tapered medicine energising chamber.
Figure 9:
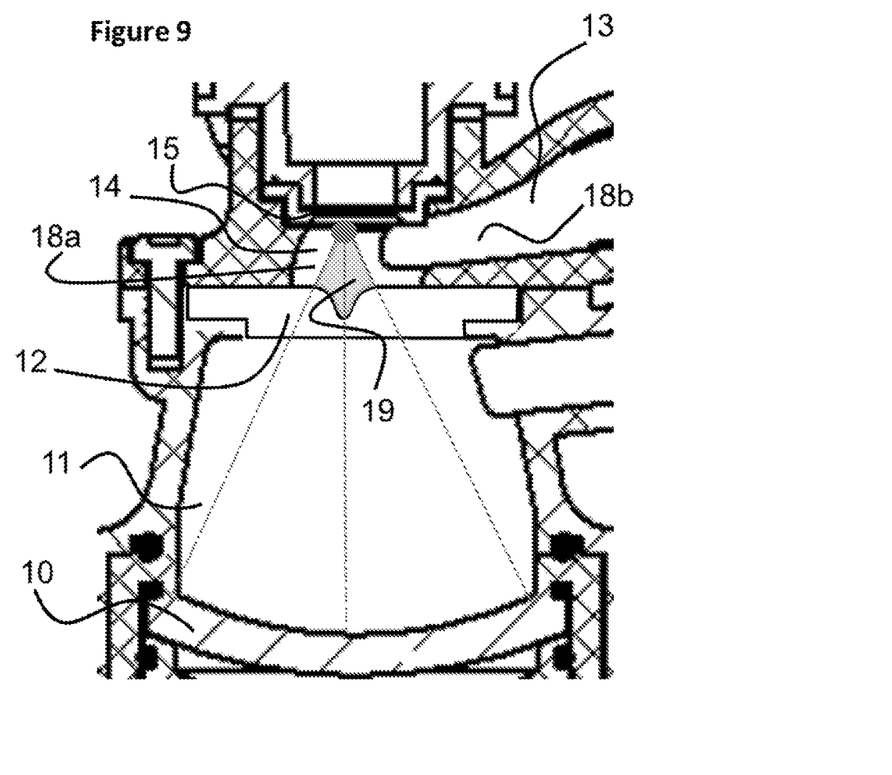
FIG. 9 is a side cross-sectional view of the medicine supply unit of an alternative embodiment of the invention showing an energising chamber which incorporates a well.

Referring to FIGS. 8 and 9, in some embodiments the energising chamber 13 has a tapered floor or a well provided by the membrane 12, designed to urge medicine 18a to gather centrally in the focal zone so as to prevent or reduce undelivered residues.

While some preferred forms of the invention have been described by way of example, it should be appreciated that modifications and improvements can occur without departing from the scope of the following claims.

The invention claimed is:

1. A delivery device for nasal medication, the device comprising:
   an ultrasonic energy generator comprising a concave transducer;
   a feeder chamber holding medication;
   an energizing chamber, smaller than the feeder chamber, holding a charge of the medication;
   an ultrasonic energy transmission medium located between the concave transducer and the energizing chamber;
   a mesh; and
   a nasal prong;
   wherein when the device is activated:
   the concave transducer causes ultrasonic energy to travel through the ultrasonic energy transmission medium towards the mesh and create a tapered focal zone of concentrated ultrasonic energy within the energizing chamber such that the charge of the medication in the energizing chamber is energized and forced from the energizing chamber so as to contact the mesh to become an aerosol and leave the device by way of the nasal prong; and
   the feeder chamber replenishes the energizing chamber with the medication so that the energizing chamber has a constant charge of the medication therewithin, but wherein when the feeder chamber is empty and the energizing chamber has an insufficient amount of the medicine from the feeder chamber to be energized and delivered via the nasal prong the insufficient amount is wastage, and wherein the smaller size of the energizing chamber relative to the feeder chamber serves to substantially limit the wastage.

2. The device according to claim 1, further comprising
   a mouthpiece for a human user to place their mouth on and blow into; and
   a breath sensor for detecting the user blowing into the mouthpiece and in response thereto causing the medication to be energized and the aerosol to form.

3. The device according to claim 1, wherein the energizing chamber has a volume of 0.1 cm$^3$ to 0.8 cm$^3$.

4. The device according to claim 1, wherein the energizing chamber has a volume of 0.2 cm$^3$ to 0.4 cm$^3$.

5. The device according to claim 1, wherein the medication in the energizing chamber becomes acoustically energized such that an acoustic radiation pressure is produced on an inner face of the mesh, resulting in oscillation of the mesh to produce a micro-pumping action with respect to the medication.

6. The device according to claim 1, wherein the mesh vibrates as the medication contacts the mesh to assist in creating the aerosol.

7. The device according to claim 1, wherein the mesh is integral with the nasal prong.

8. The device according to claim 7, wherein the nasal prong includes an exit, and the mesh is immediately adjacent to the exit and is configured to minimize condensation of the aerosol inside the device.

9. The device according to claim 8, wherein the energizing chamber, the ultrasonic energy generator and the exit are at an angle of about 40° to about 80° with respect to the mouthpiece.

10. The device according to claim 8, wherein the energizing chamber, the ultrasonic energy generator and the exit are at an angle of about 50° to about 70° with respect to the mouthpiece.

11. The device according to claim 1, wherein the medication is a pharmaceutical or saline solution.

12. The device according to claim 1, wherein the feeder chamber has a funnel or flume that naturally encourages the medication into the energizing chamber.

13. The device according to claim 1, wherein the energizing chamber has a tapered floor that urges the medication to gather at the tapered focal zone.

14. The device according to claim 1, wherein the energizing chamber has a well that urges the medication to gather at the tapered focal zone.

15. The device according to claim 1, wherein the feeder chamber plus the energizing chamber collectively have sufficient medication for one of:
   only 5 or fewer patient doses;
   only 4 or fewer patient doses;
   only 3 or fewer patient doses;
   only 2 or fewer patient doses; and
   only 1 patient dose.

16. The device according to claim 1, wherein the feeder chamber is at one side of the device only, detachably cantilevers outwardly, and is tilted upwardly from, a location between the nasal prong and the ultrasonic energy generator.

17. The device according to claim 1, wherein:
   the tapered focal zone extends from a floor of the energizing chamber to a roof of the energizing chamber;
   the concave transducer acoustically energizes the charge of the medication within the tapered focal zone to produce an acoustic radiation pressure on an inner face of the mesh so that the mesh oscillates to cause a micro-pumping action of the medication as it moves through the mesh; and
   the feeder chamber is at one side of the device only, detachably cantilevers outwardly from a location between the nasal prong and the ultrasonic energy generator.

18. The device of claim 1, wherein the feeder chamber is located between the nasal prong and the concave transducer.

19. The device of claim 1, wherein the feeder chamber replenishes the energizing chamber with the medication by way of gravity acting on the medication.

20. A delivery device for nasal medication, the device comprising:
   a mouthpiece to contact a mouth of a user;
   a breath sensor;
   an ultrasonic energy generator comprising a concave transducer;
   a feeder chamber holding medication;
   an energizing chamber smaller than the feeder chamber;
   a mesh; and
   a nasal prong;
   wherein when the device is activated:
   the concave transducer causes ultrasonic energy to travel toward the mesh and create a tapered focal zone of concentrated ultrasonic energy within the energizing chamber such that a charge of the medication in the energizing chamber is energized and forced from the energizing chamber so as to contact the mesh to become an aerosol and leave the device by way of the nasal prong;
   the feeder chamber replenishes the energizing chamber with the medication so that the energizing chamber has a substantially constant charge of the medication therewithin, but wherein when the feeder chamber is empty and the energizing chamber has an insufficient amount of medicine from the feeder chamber to be energized and delivered via the nasal prong this insufficient amount is wastage, and wherein the smaller size of the energizing chamber relative to the feeder chamber serves to substantially limit the wastage; and the breath sensor detects a user blowing into the mouthpiece and in response thereto causes the medication in the energizing chamber to be energized while the mesh oscillates to produce a micro-pumping action to assist in creating the aerosol.

21. The device according to claim 20, wherein the medication in the energizing chamber is acoustically energized within the tapered focal zone such that an acoustic radiation pressure is produced on an inner face of the mesh, resulting in the oscillation of the mesh to produce the micro-pumping action with respect to the medication.

22. The device of claim 20, wherein the feeder chamber is cantilevered outwardly between the nasal prong and the concave transducer.

23. The device of claim 20, wherein the feeder chamber is located between the nasal prong and the concave transducer and is angled upward from the energizing chamber towards the nasal prong to prevent bubbles from forming.

24. A delivery device for nasal medication, the device comprising:

an ultrasonic energy generator that creates a tapered ultrasonic focal zone of concentrated ultrasonic energy;

an ultrasonic energy transmission medium;

an energizing chamber holding medication at the tapered ultrasonic focal zone, wherein the energizing chamber is remote from the ultrasonic energy generator;

a feeder chamber larger than the energizing chamber and capable of holding more of the medication, wherein the feeder chamber continuously fills the energizing chamber with medication so that there is a substantially constant supply of the medication within the tapered ultrasonic focal zone;

a mesh; and a nasal prong;

wherein the feeder chamber detachably cantilevers outwardly from one side of the device at a location between the nasal prong and the ultrasonic energy generator; and wherein when the device is activated:

ultrasonic energy travels through the ultrasonic energy transmission medium towards the tapered ultrasonic focal zone; and the medicine within the tapered ultrasonic focal zone is energized and forced from the energizing chamber so as to contact the mesh, become an aerosol, and leave the device by way of the nasal prong.

* * * * *